US006949353B2

(12) United States Patent
Romette et al.

(10) Patent No.: US 6,949,353 B2
(45) Date of Patent: Sep. 27, 2005

(54) CAPPING ENZYME OF FLAVIVIRUS AND UTILIZATION OF THIS PROTEIN IN A PROCESS TO TEST DRUGS WITH ANTIVIRAL PROPERTIES

(75) Inventors: Jean-Louis Romette, Marseilles (FR); Delphine Benarroch, Marseilles (FR); Bruno Canard, Cassis (FR); Marie-Pierre Egloff, Marseilles (FR)

(73) Assignee: Centre National de la Recherche Scientifique, C.N.R.S. (FR)

( * ) Notice: Subject to any disclaimer, the term of this patent is extended or adjusted under 35 U.S.C. 154(b) by 0 days.

(21) Appl. No.: 10/160,821

(22) Filed: May 31, 2002

(65) Prior Publication Data

US 2005/0100882 A1 May 12, 2005

Related U.S. Application Data

(60) Provisional application No. 60/294,804, filed on May 31, 2001.

(51) Int. Cl.[7] ............................ C12Q 1/48; C12Q 1/70; C12N 9/10

(52) U.S. Cl. ............................ 435/15; 435/5; 435/193; 435/235.1; 530/350

(58) Field of Search ............................ 435/193, 235.1, 435/5, 15; 530/350

(56) References Cited

U.S. PATENT DOCUMENTS

2002/0164348 A1 * 11/2002 Kirkegaard et al. ..... 424/186.1

OTHER PUBLICATIONS

Steffens et al (Journal of General Virology 80:2583–2590, 1999).*

Raviprakash et al (American Journal of Tropical Medicine and Hygiene 58:90–95, 1998).*

Koonin (Journal of General Virology 74:733–740, 1993).*

Leyssen et al (Clinical Microbiology Reviews 13:67–82, 2000).*

* cited by examiner

*Primary Examiner*—Mary E. Mosher
(74) *Attorney, Agent, or Firm*—DLA Piper Rudnick Gray Cary US LLP

(57) ABSTRACT

This invention concerns an isolated and purified polypeptide capable of acting as a guanylyltransferase and methyltransferase comprising capping enzyme of *flavivirus* (CEF). The invention also concerns the use of such polypeptide to identify biologically active molecule wich can be used in the treatment or the prevention of diseases resulting from *Flavivirus* infection.

16 Claims, 8 Drawing Sheets

(4 of 8 Drawing Sheet(s) Filed in Color)

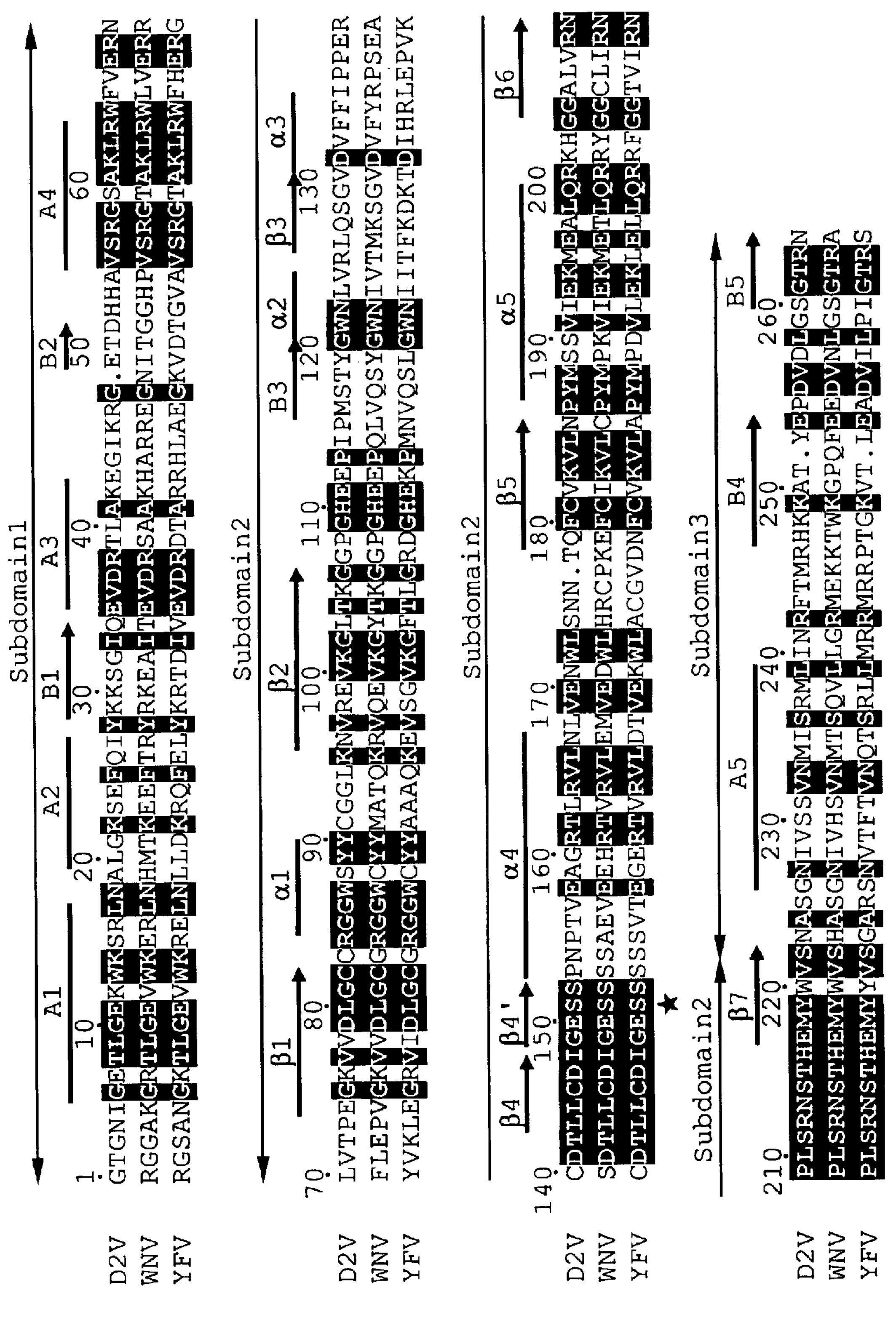

FIG. 2B

Subdomain1

```
            A1                    A2               B1            A3                  B2             A4
            →                     →                →             →                   →              →
        1         10        20          30           40            50          60
D2V     GTGNIGETLGEKWKSRLNALGKSEFQIYKKSGIQEVDRTLAKEGIKRG.ETDHHAVSRGSAKLRWFVERN
WNV     RGGAKGRTLGEVWKERLNHMTKEEFTRYRKEAITEVDRSAAKHARREGNITGGHPVSRGTAKLRWLVERR
YFV     RGSANCKTLGEVWKRELNLLDKRQFELYKRTDIVEVDRDTARRHLAECKVDTGVAVSRGTAKLRWFHERG
```

Subdomain2

```
              β1              α1                β2              β3    α2            β3    α3
              →               →                 →               →     →             →     →
        70          80           90         100          110         120          130
D2V     LVTPECKVDLGCGRGGWSYYCGGLKNVREVKGLTKGGPGHEEPIPMSTYGWNLVRLQSGVDVFFIPPER
WNV     FLEPVGKVDLGCGRGGWCYYMATQKRVQEVKGYTKGGPGHEEPQLVQSYGWNIVTMKSGVDVFYRPSEA
YFV     YVKLEGRVIDLGCGRGGWCYYAAAQKEVSGVKGFTLGRDGHEKPMNVQSLGWNIITFKDKTDIHRLEPVK
                                                                              ★
```

Subdomain2

```
         β4      β4'            α4                             β5              α5
         →       →              →                              →               →
       140           150          160          170          180          190          200
D2V    CDTLLCDIGESSPNPTVEAGRTLRVLNLVENWLSNN.TQFCVKVLNPYMSSVIEKMEALQRKHGGALVRN
WNV    SDTLLCDIGESSSAEVEEHRTVRVLEMVEDWLHRCPKEFCIKVLCPYMPKVIEKMETLQRRYGGCLIRN
YFV    CDTLLCDIGESSSSVTEGERTVRVLDTVEKWLACGVDNFCVKVLAPYMPDVLEKLELLQRRFGGTVIRN
```

Subdomain3

```
           β7                           A5             B4               B5           β6
           →                            →              →                →            →
        210         220          230          240          250          260
D2V     PLSRNSTHEMYWVSNASGNIVSSVNMISRMLINRFTMRHKKAT.YEPDVDLGSGTRN
WNV     PLSRNSTHEMYWVSHASGNIVHSVNMTSQVLLGRMEKKTWKGPQFEEDVNLGSGTRA
YFV     PLSRNSTHEMYYVSGARSNVTFTVNQTSRLLMRRMRRPTGKVT.LEADVILPIGTRS
```

| y = m1 * M0/(m2 + M0) | | |
|---|---|---|
| | Value | Error |
| Saturation (CPM) | 1297.7 | 196.2 |
| Kd(GTP) (μM) | 52.158 | 24.575 |
| Chisq | 1.0268e†05 | NA |
| R | 0.95911 | NA |

| y = m1 * M0/(m2 + M0) | | |
|---|---|---|
| | Value | Error |
| Saturation (%) | 73.001 | 1.314 |
| Rel. $Kd_{(acyclo-TP)}$ (μM) | 79.771 | 7.234 |
| Chisq | 7.6423 | NA |
| R | 0.99885 | NA |

CAPPING ENZYME OF FLAVIVIRUS AND UTILIZATION OF THIS PROTEIN IN A PROCESS TO TEST DRUGS WITH ANTIVIRAL PROPERTIES

RELATED APPLICATION

This patent application claims the benefit of U.S. Provisional Application No. 60/294,804, filed May 31, 2001. This earlier provisional application is hereby incorporated by reference.

FIELD OF THE INVENTION

This invention is in the field of antiviral molecular biology. Particularly, this invention relates to the capping enzyme of *Flavivirus* and nucleoside analogues that competitively bind to these polypeptides.

BACKGROUND

The cap is a unique structure found at the 5'-end of viral and cellular eukaryotic mRNA (1). This cap is critical for both mRNA stability and binding to the ribosome during translation. mRNA capping is a co-transcriptional modification resulting from a series of three chemical reactions (2). The 5'-triphosphate of the mRNA is first converted to a diphosphate by an RNA triphosphatase. The second reaction is a transfer of a GMP moiety from GTP to the 5'-diphosphate RNA by the guanylyltransferase (capping enzyme) to yield $G^{5'}$-$ppp^{5'}$-N. In general, this reaction involves a covalent attachment of the a-phosphate of GTP to the e-$NH_2$ group of a lysine residue to yield a phosphoramide (P—N) bond with the concomitant release of pyrophosphate. In a third reaction utilizing S-adenosyl-L-methionine as the methyl donor, the transferred guanosine moiety is methylated by a methyltransferase at its N7 position to yield $^{7Me}G^{5'}$-$ppp^{5'}$-N (cap 0 structure). In some instances, a second methyl transfer reaction methylates the 2'-OH of the first nucleotide 3' to the triphosphate bridge to yield $^{7Me}G^{5'}$-$ppp^{5'}$-$N_{2'OMe}$ (cap 1 structure) and it is the case for the mRNA Dengue virus.

Many viruses replicate in the cytoplasm of their eukaryotic host. Since cellular RNA capping is localized in the nucleus, these viruses often encode their own capping enzymes while relying on the host translation machinery for gene expression. Although the physical organization of the capping apparatus has diverged in cellular and viral systems, eukaryotic cellular and DNA virus guanylyltransferases have been grouped into a superfamily of covalent nucleotidyltransferases on the basis of structural and mechanistic features (3).

The crystal structure of the DNA virus PBCV-1 (Chlorella virus) guanylyltransferase in complex with GTP has illuminated the structural and mechanistic determinants of guanylyl transfer in this enzyme family (4). Covalent attachment of GMP to the enzyme is a hallmark of guanylyltransferase activity in this family. Unlike DNA viruses, however, the classification and mechanism of RNA virus guanylyltransferases is elusive. Only a few guanylyltransferase activities from RNA viruses have been assigned to viral proteins because they do not share obvious amino acid sequence homology with covalent nucleotidyltransferases. The sole example of a structurally defined RNA virus guanylyltransferase is the crystal structure of the Reovirus core at 3.6 Å resolution comprising the λ2 subunit (5). However, it is a double strand-RNA virus, and not a single strand-RNA virus. As RNA capping is essential for several viruses (6), it is a potential target for antiviral design.

The guanosine analogue Ribavirin is a broad spectrum antiviral agent discovered about thirty years ago (7). Its mechanism of action has remained controversial (8). Like most nucleoside analogues, Ribavirin is phosphorylated at its 5'-position upon penetration into the cell. Ribavirin 5'-monophosphate is a potent inhibitor of the cellular enzyme inosine 5'-monophosphate dehydrogenase (IMP-DH). This inhibition results in depletion of the intracellular guanosine nucleotide pool which feeds capping and polymerase enzymes of both viral and cellular origin. Consequently, the Ribavirin-depressed guanosine nucleotide pool may exert an indirect antiviral effect because viral enzymes would not compete advantageously for guanosine nucleotide with cellular enzymes. In addition, Ribavirin nucleotides might have a viral target, such as RNA capping, responsible for the observed antiviral effect (reviewed in (8)), but direct evidence for this mechanism was lacking. Elucidation of the Ribavirin mechanism of action has been plagued by the possible involvement of both direct and indirect mechanisms.

Viruses from the *Flaviviridae* family are sensitive to Ribavirin (9, 10). The genus *Flavivirus* comprises important human pathogens such as West Nile, Dengue and Yellow Fever viruses. These mosquito-borne viruses are currently expanding their distribution over the world. West Nile virus introduction in North America may be an important milestone in the evolving history of this virus, as exemplified with recent outbreaks in the New-York area (11). The Camargue area in France has re-witnessed West Nile virus infection of horses after 40 years. Likewise, Dengue virus, an agent responsible for hemorrhagic fever, is infecting more than 50 million persons annually with an increasing incidence in tropical areas around the world.

The *Flavivirus* single-stranded RNA genome is of positive polarity, and capped with a cap 1 structure (12). The guanylyltransferase has not yet been identified. Structural insights into viral RNA capping and its inhibition may reveal a putative target for Ribavirin and help the identification and design of inhibitors directed against *Flaviviruses.* Once identified, such inhibitors will be useful in the treatment of diseases resulting from *Flavivirus* infection.

This invention discloses an isolated and purified polypeptide capable of acting as a guanylyltransferase and methyltransferase comprising capping enzyme of *flavivirus* (CEF). The polypeptide of the invention comprises a N-terminal module (subdomain 1), a SAM-binding core (subdomain 2), and a C-terminal sequence (subdomain 3) located between subdomains 1 and 2, and forming the bottom of a narrow cleft. The subdomain 1 of the polypeptide of the invention starts with a helix A1-turn-helix A2 motif. The subdomain 2 polypeptide of the invention is comprised of a twisted mixed β-sheet comprising 7 β-strands (β1 to β7) and 5 helices (α1 to α5) and its subdomain 3 is positively charged.

The polypeptide of the invention is designated "CEF" (Capping Enzyme of *Flavivirus*). This invention provides the general structure of CEF. The amino acid sequences of three CEFs—for the Dengue virus, the West Nile Virus, and Yellow Fever Virus—are also disclosed and these sequences are respectively represented by SEQ ID No. 1, SEQ ID No. 2 and SEQ ID No. 3 in the sequence listing in the appendix.

The invention relates to polypeptides homologous to a polypeptide whose amino acid sequence is represented by SEQ ID No. 1, SEQ ID No. 2 or SEQ ID No. 3. More particularly, the invention relates to polypeptides which have at least about 95% homology with amino acid sequences represented by SEQ ID No. 1, SEQ ID No. 2 or SEQ ID No. 3.

The invention also concerns a nucleic acid molecule comprising or constituted of an encoding nucleic sequence for a polypeptide capable of acting as a guanylyltransferase and methyltransferase comprising capping enzyme of *flavivirus* (CEF). The invention also concerns nucleotide sequences derived from the above sequences, for example, from the degeneracy of the genetic code, and which encode for proteins having characteristics and properties of CEF.

The invention includes polyclonal or monoclonal antibodies directed against a polypeptide of the invention, a derivative or a fragment thereof. These antibodies can be prepared by known methods. The antibodies are useful in identifying new CEF or the homologues of this enzyme in other virus belonging to the *flavivirus* genus.

The invention also concerns a vector comprising at least one molecule of the nucleic acid above, advantageously associated with adapted control sequences, together with a production or expression process in a cellular host of the CEF of the invention or a fragment thereof. The preparation of these vectors as well as the production or expression in a protein host of the invention can be carried out by molecular biology and genetic engineering techniques well known to the one skilled in the art.

An encoding nucleic acid molecule for a polypeptide capable of acting as a guanylyltransferase and methyltransferase comprising capping enzyme of *flavivirus* (CEF) or a vector according to the invention can also be used to transform animals and establish a line of transgenic animals. The vector used is chosen in function of the host into which it is to be transferred. It can be any vector such as a plasmid. Thus, the invention also relates to cellular hosts expressing a polypeptide capable of acting as a guanylyltransferase and methyltransferase comprising capping enzyme of *flavivirus* (CEF) obtained in conformity with the preceding processes.

The invention also relates to nucleic and oligonucleotide probes prepared from the molecules of nucleic acid according to the invention. These probes, marked advantageously, are useful for hybridisation detection of CEF in other viruses of the *Flavivirus* genus. According to prior art techniques, these probes are put into contact with a biological sample. Different hybridization techniques can be used, such as Dot-blot hybridisation or replica hybridisation (Southern technique) or other techniques (DNA chips). Such probes constitute the tools making it possible to detect similar sequences quickly in the encoding genes of different virus of the *Flavivirus* genus. The oligonucleotide probes are useful for PCR experiments, for example, in a diagnostic sense.

The invention can also be useful in methods for determining the inhibitory power of a biologically active compound acting as a competitive inhibitor of GTP comprising:

a) incubating CEF with radiolabeled GTP, b) adding selected different concentrations of the biologically active compound, c) assaying resulting radiolabeled CEF-GTP complex produced from the incubation, d) quantifying an amount of radiolabeled CEF-GTP complex produced from the assay, e) comparing the amount to a binding affinity constant of GTP to CEF, and f) determining the inhibitory power of the biologically active compound.

More particularly, the incubating step in the methods of the invention is conducted at about 52 $\mu$M of GTP. Selected different concentrations of GTP are about 0 $\mu$M, about 10 $\mu$M, about 20 $\mu$M, about 50 $\mu$M, about 100 $\mu$M, about 200 $\mu$M, about 300 $\mu$M, about 500 $\mu$M, and about 800 $\mu$M. Assaying in the methods of the invention comprises UV-crosslinking of $\alpha$-$^{32}$P-GTP to CEF.

The invention relates to methods for selecting an inhibitory biologically active compound capable of reducing CEF binding to GTP as an antiviral pharmaceutical agent comprising selecting biologically active compounds with a binding affinity higher than the binding affinity constant of GTP to CEF.

The biologically active compound which can be used in the methods of the invention can be a nucleoside, a nucleoside analogue or a non-nucleoside molecule, for example.

We discovered that the triphosphate form of acyclovir and a vectorized form of acyclovir 5'-monophosphate are good inhibitors of the CEF enzyme. Thus, the invention concerns the use of acyclovir 5'-triphosphate or a vectorized form of acyclovir 5'-monophosphate for preparing a medicine useful in treating or preventing diseases resulting from *Flavivirus* infection. The terms "vectorized form" relates to any vector capable of transporting acyclovir 5'-monophosphate to a particular cell such as an infected cell and to introduce acyclovir 5'-monophosphate into the cell. All kinds of vectors known by those skilled in the art can be used in the invention.

BRIEF DESCRIPTION OF THE DRAWINGS

The patent application file contains at least one drawing executed in color. Copies of this patent application publication with color drawings will be provided by the Office upon request and payment of the necessary fee.

Other advantages and characteristics of the invention will become apparent by reading the following examples concerning the identification of the *Flavivirus* capping enzyme, its structure and its activity and which refer to the attached drawings in which:

FIG. 1A shows cross-linking of $\alpha$-$^{32}$P-GTP to CEF.

FIG. 2B is three sequence listings of the CEF of three *Flaviviruses*. Specifically, SEQ ID No. 1 is the four lines designated D2V, SEQ ID No. 2 is the four lines designated WNV, and SEQ ID No. 3 is the four lines designated YFV.

DETAILED DESCRIPTION

Figure 1A:
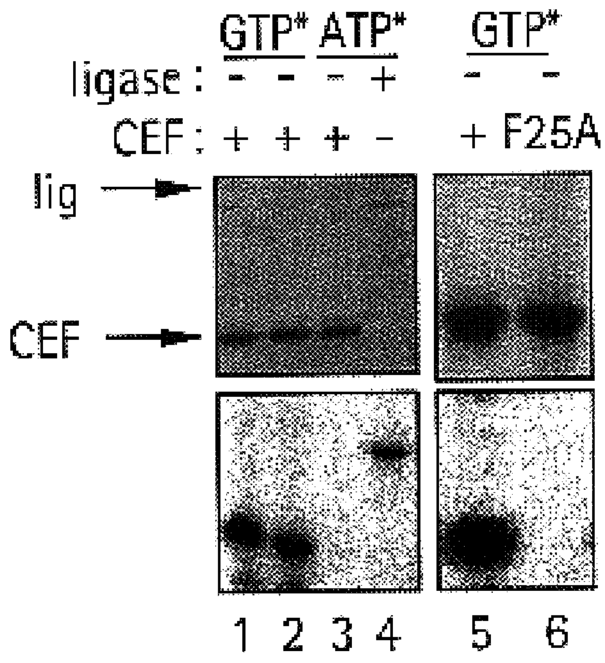
FIGS. 1A and B are a pair of photographs of gel electrophoresis.
Figure 1B:
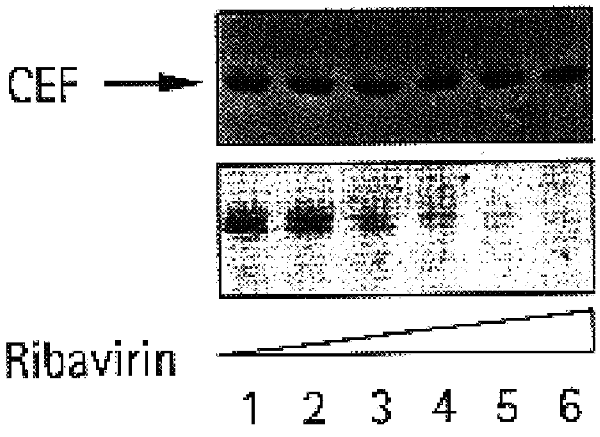
FIG. 1B shows competition of Ribavirin 5'-triphosphate with GTP for covalent binding to CEF.

In the drawings, as noted above, FIGS. 1A and 1B are a pair of photographs of gel electrophoresis. FIG. 1A shows cross-linking of α-$^{32}$P-GTP to CEF. 2 μg of CEF was incubated with 50 μM (1 μCi) of either α-$^{32}$P-GTP (lane 1, 2, 5, 6) or α-$^{32}$P-ATP (lanes 3, 4) in 50 mM Tris pH 7.6, 5 mM DTT in the presence (lane 1, 3–6)) or absence (lane 2) of 5 mM $Mg^{2+}$. The sample was cross-linked using UV irradiation (254 nm), boiled for 5 min, and subjected to denaturing gel electrophoresis. Products were analyzed and quantified using photostimulable plates and a FujiImager. Bacteriophage T4 DNA ligase served as a positive control (lane 5). The F25A variant of CEF was purified under the same conditions as those of wild-type CEF. Upper panels show the comassie-blue stained gels, and lower panels the corresponding autoradiographic analysis. FIG. 1B shows competition of Ribavirin 5'-triphosphate with GTP for covalent binding to CEF. CEF was incubated during 10 min with increasing concentrations of Ribavirin 5'-triphosphate (0–50–250–500–750–1000 μM, lanes 1- to 6, respectively) before addition of α-$^{32}$P-GTP to the reaction mixture and further incubation for 20 min. The mixture was boiled for 5 min, subjected to denaturing gel electrophoresis, and the gel analyzed and quantified as in panel A. Upper panels show the comassie-blue stained gels, and lower panels the corresponding autoradiographic analysis. Ribavirin: Ribavirin 5'-triphosphate; Lig: Bacteriophage T4 DNA ligase.

Figure 2A:
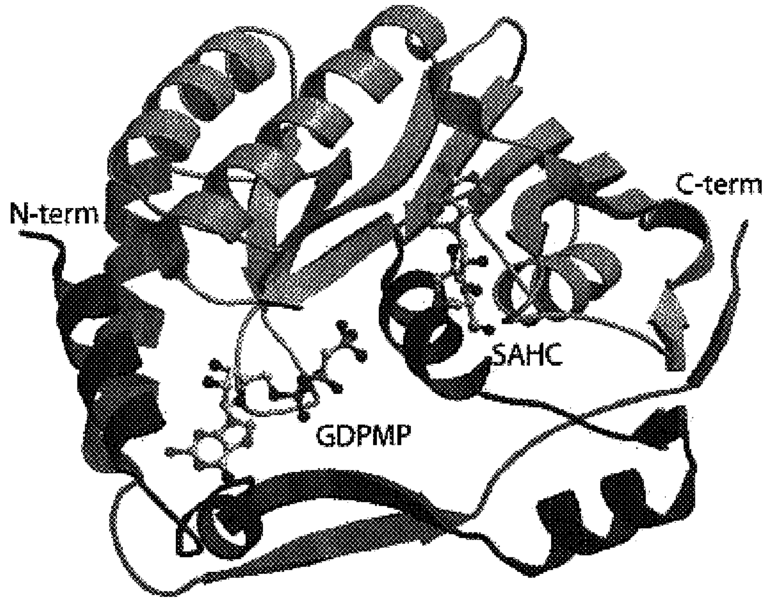
FIG. 2A is a schematic representation of the crystal structure of CEF in complex with SAHC and GDPMP.

FIG. 2A is a schematic representation of the crystal structure of CEF in complex with SAHC and GDPMP. A ball-and-stick representation is used for both SAHC and GDPMP molecules, whereas CEF is drawn as a ribbon. The core of CEP (residues 71 to 222, colored in gold) consists of a seven-stranded b-sheet (b1 to b7), surrounded by 5 helices (a1 to a5). This fold is shared by a number of SAM-dependent methyltransferases. Appended to the N-terminus of the core is the 70 residue modular extension (colored in red) responsible for the binding of the GTP analogue. The actual interactions with the base and ribose of the nucleotide are made by an helix-turn-helix motif (helices A1 and A2). The C-terminal part of CEF (residues 223 to 264, colored in cyan) folds against the N-terminal region (helix A5 packs against A1, and strand B4 makes hydrogen bonds with B1). The figure was generated using MOLSCRIPT (28) and rendered using RASTER3D (29).

FIG. 2B is three sequence listings of the CEF of three *Flaviviruses*. Specifically, SEQ ID No. 1 is the four lines designated D2V, SEQ ID No. 2 is the four lines designated WNV, and SEQ ID No. 3 is the four lines designated YFV. The sequence listings are also more particularly set forth as follows:

SEQ ID No. 1—Dengue virus type 2 GTGNIGETLGEK WKSRLNALGKSEFQIYKKSGIQEVDRTLAKEGIK RGETDHHAVSRGSAKLRWFVERNLVTPEGKVV DLGCCRGGWSYYCGGLKNVREVKGLTKGGPGH EEPIPMSTYGWNLVRLQSGVDVFFIPPERCDTLLCDI GESSPNPTVEAGRTLRVLNLVENWLSNNTQFCVKV LNPYMSSVTEKMEALQRKFGGALVRNPLSRNSTHE MYWVSNASGNIVSSVNMISRMLINRFTMRHKKAT YEPDVDL GSGTRN SEQ ID No. 2—West Nile virus RGGAKGRTLGEVWKERLNEMTKEEFTRYRKEAIIE VDRSAAKHARREGNITGGHPVSRGTAKLRWLVER RFLEPVGKVVDLGCGRGGWCYYMATQKRVQEVK GYTKGGPGHEEPQLVQSYGWNIVTMKSGVDVFYR PSEASDTLLCDIGESSSSAEVEEHRTVRVLEMVED WLHRGPKEFCIKVLCPYMPKVIEKMEILQRRYG GGLIRNPLSRNSTHEMYWVSHASGNIVHSVNMT SQVLLGRMEKKTWKGPQFEEDVNLGSGTRA SEQ ID No. 3—Yellow Fever Virus RGSANGKTLGEVWKRELNLLDKRQFELYKRTDIV EVDRDTARRHLAEGKVDTGVAVSRGTAKLRWFHER GYVKLEGRVIDLGCGRGGWCYYAAAQKEVSGVKG FTLGRDGHEKPMNVQSLGWNIITFKDKTDIHRLEP VKCDTLLCDIGESSSSSVTEGERTVRVLDTVEKW LACGVDNFCVKVLAPYMPDVLEKLELLQRRFG GTVIRNPLSRNSTHEMYYVSGARSNVTFTVNQTSR LLMRRMRRPTGKVTLEADVILPIGTRS Structure-based alignment colored according to the ribbon representation of CEF. CEF domains from Dengue virus type 2 New Guinea isolate (D2V), West Nile virus New York isolate (WNV), and Yellow Fever 17D (YFV) were aligned using CLUSTALW and rendered using ESPript. Secondary structures (a-helices and b-strands) of subdomains 1, 2, and 3 are indicated above the alignment and colored in red, gold, and cyan, respectively. Helices and strands are named using greek letters inside the core domain (subdomain 2), and roman letters outside (subdomains 1 and 3). Amino acids involved in nucleoside 5'-triphosphate binding are indicated by a star below aligned sequences (see text).

Figure 2C:
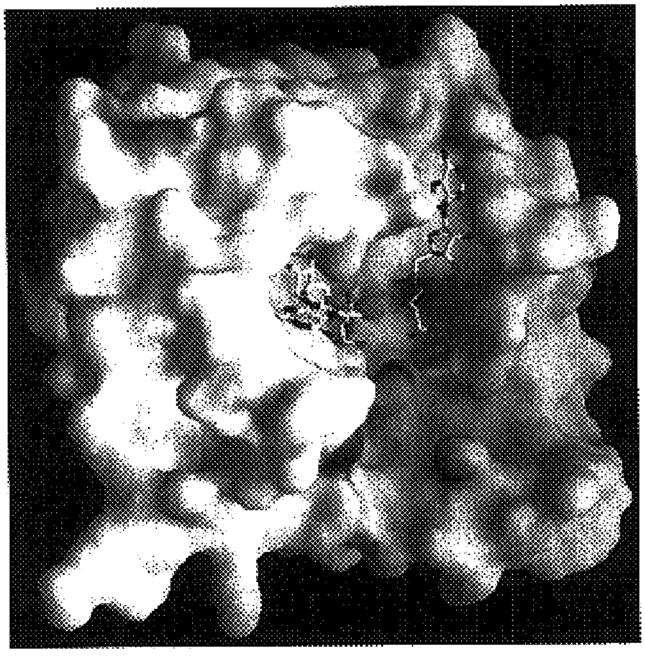
FIG. 2C is a schematic representation of the surface potential of CEF.

FIG. 2C is a schematic representation of the surface potential of CEF. Regions of the surface exhibiting negative and positive net charge are colored in red and blue, respectively. The figure was generated using GRASP (30). Both SAHC and GDPMP are displayed in sticks in the cleft bisecting the surface of CEF.

Figure 3A:
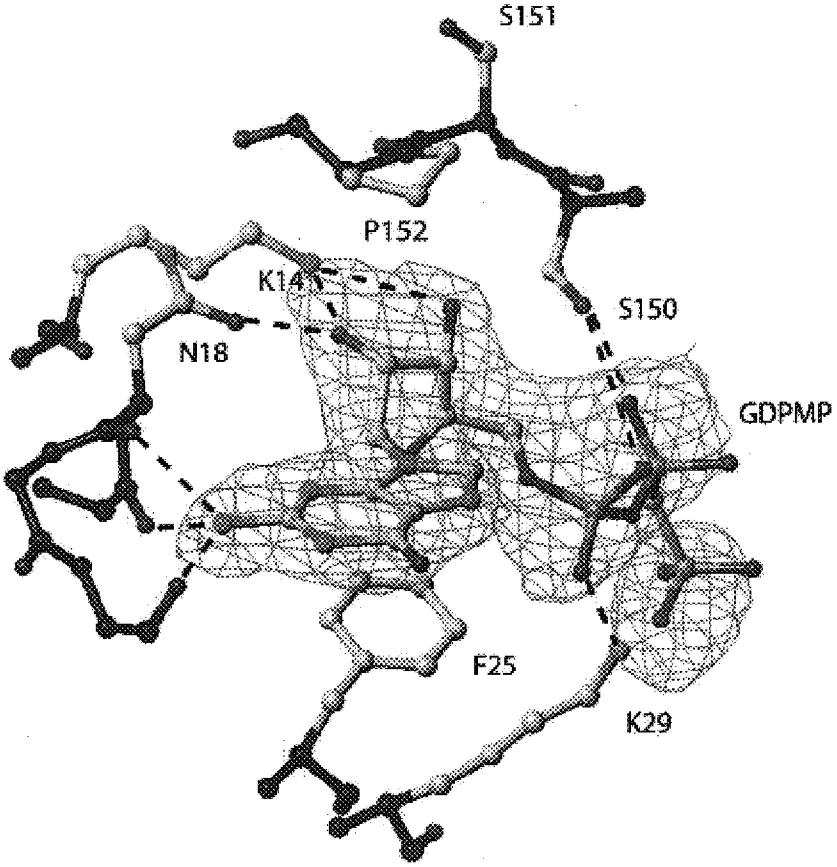
FIG. 3A is a ball-and-stick representation of the nucleotide binding site of CEF.

FIG. 3A is a ball-and-stick representation of the nucleotide binding site of CEF. Experimental (Fo-Fc) difference map (2.8 Å) contoured at 3s in the vicinity of F25 in a GDPMP-soaked crystal. Although the electron density corresponding to the methylene bond bridging the b and g phosphates of GDPMP is weak, the a, b, and g phosphate positions are well defined (6s in the initial difference Fourier map). Residues interacting with GDPMP are shown in ball-and-stick. Main-chain carbon atoms are colored in dark blue except for the carbonyl oxygens colored in red; side-chains are colored according to atom-type. For clarity, non-interacting side-chains of residues 17, 19, and 20 are not shown. Dotted lines indicate hydrogen bonds.

Figure 3B:
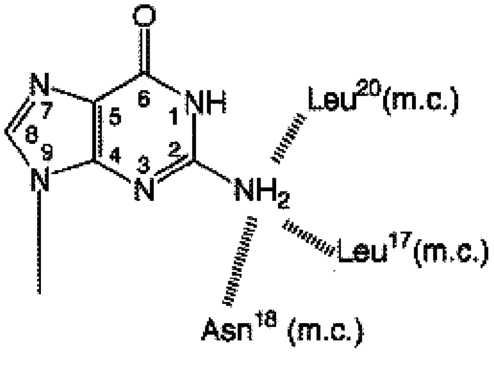
FIG. 3B is a schematic diagram showing guanine with CEF residues. Dotted lines indicate hydrogen bonds.

FIG. 3B is a schematic diagram showing guanine with CEF residues. Dotted lines indicate hydrogen bonds.

Figure 4A:
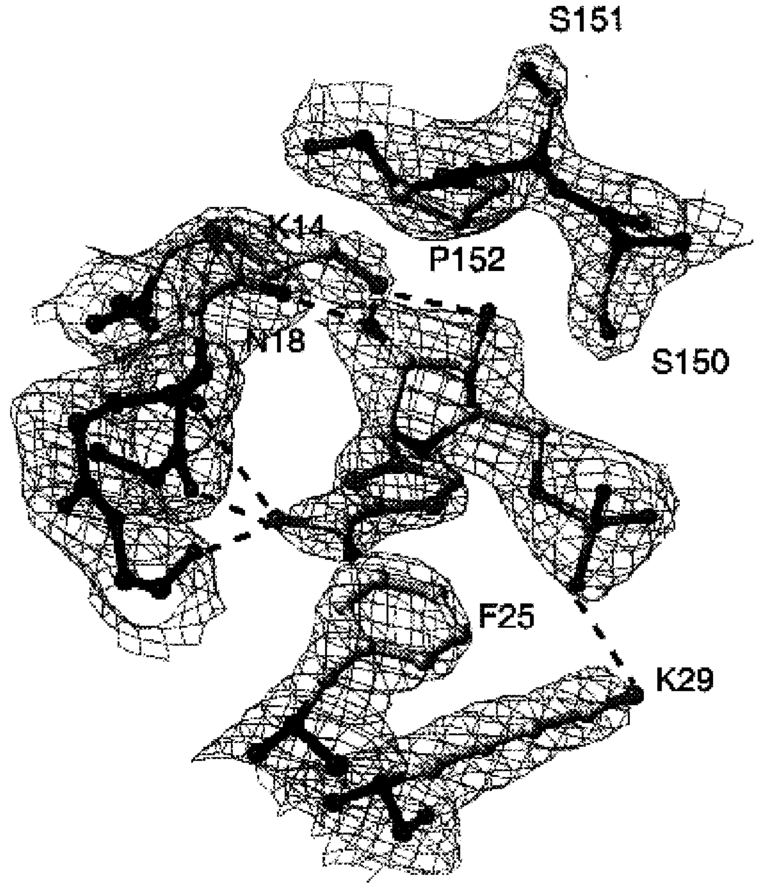
FIG. 4A is a ball-and-stick representation of Ribavirin nucleotide bound to CEF.

FIG. 4A is a ball-and-stick representation of Ribavirin nucleotide bound to CEF. A refined density map is around the Ribavirin nucleotide at 2.4 Å resolution. A CEF crystal was soaked in a solution containing 4 mM Ribavirin 5'-triphosphate. The b and g phosphate densities are absent from the initial difference Fourier map. Shown is the (3Fo-2Fc) electron density map, contoured at is around the refined Ribavirin 5'-monophosphate molecule. Dotted lines indicate hydrogen bonds.

Figure 4B:
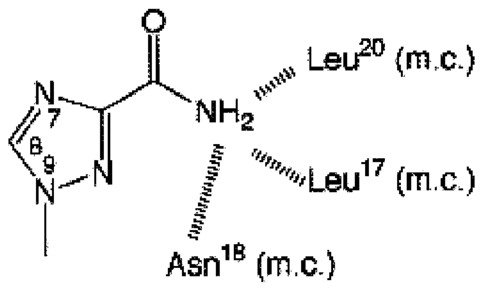
FIG. 4B is a schematic diagram showing the Ribavirin pseudo-base with CEF residues. Dotted lines indicate hydrogen bonds.

FIG. 4B is a schematic diagram showing the Ribavirin pseudo-base with CEF residues. Dotted lines indicate hydrogen bonds.

Figure 5A:
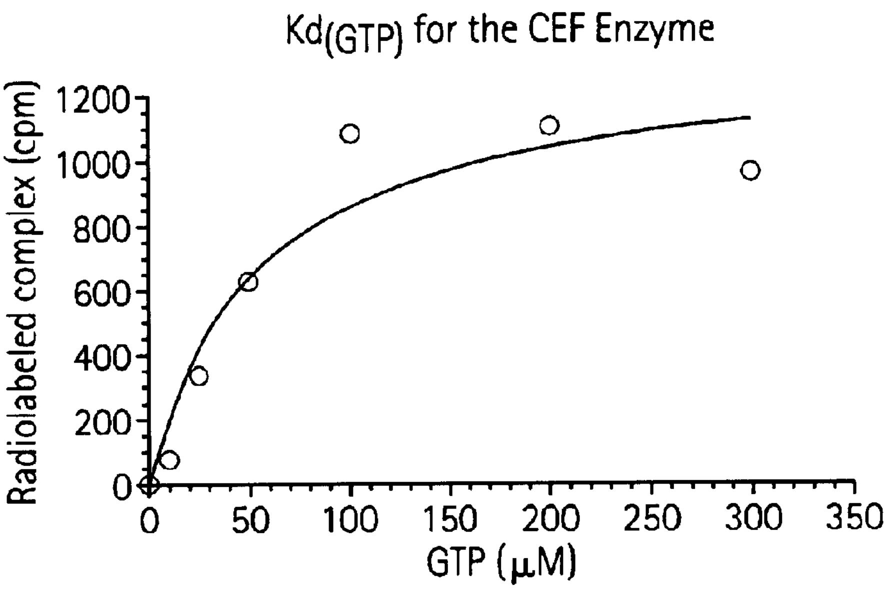
FIG. 5A is a graph showing the binding of CEF to GTP as a function of increasing concentrations of GTP.

FIG. 5A is a graph showing the binding of CEF to GTP as a function of increasing concentrations of GTP.

Figure 5B:
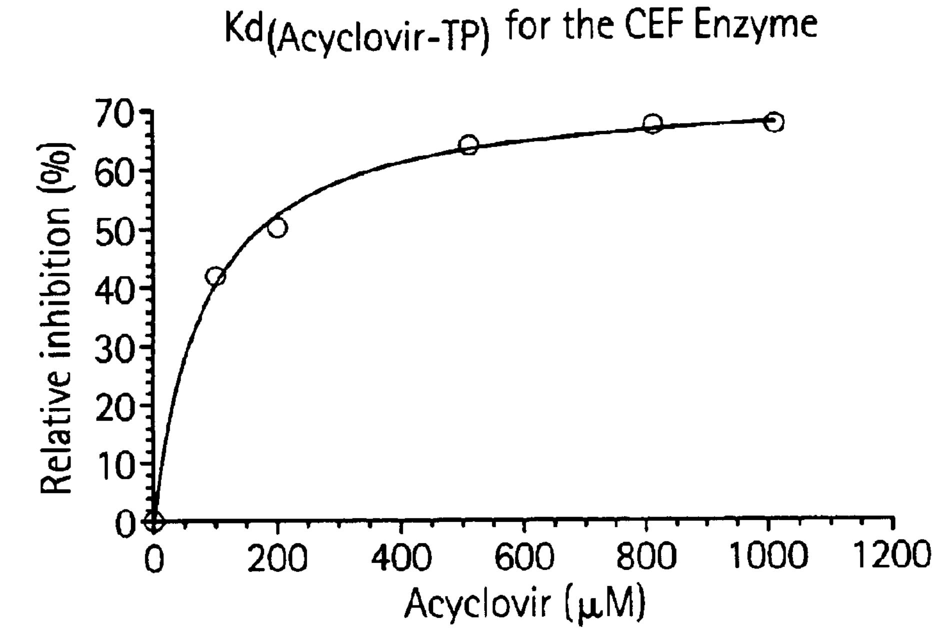
FIG. 5B is a graph showing the relative inhibition of CEF binding to GTP as a function of increased concentrations of Acyclovir 5'-triphosphate.

FIG. 5B is a graph showing the relative inhibition of CEF binding to GTP as a function of increased concentrations of Acyclovir 5'-triphosphate.

Figure 6A:
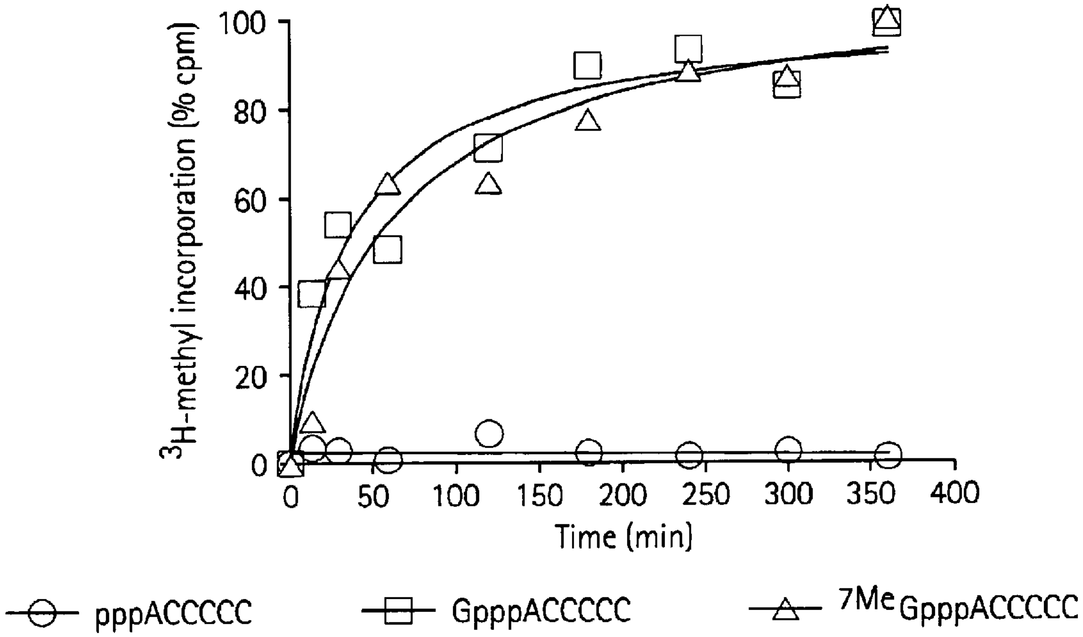
FIG. 6 concerns the MTase activity. (A) Assay of the MTase activity.
Figure 6B:
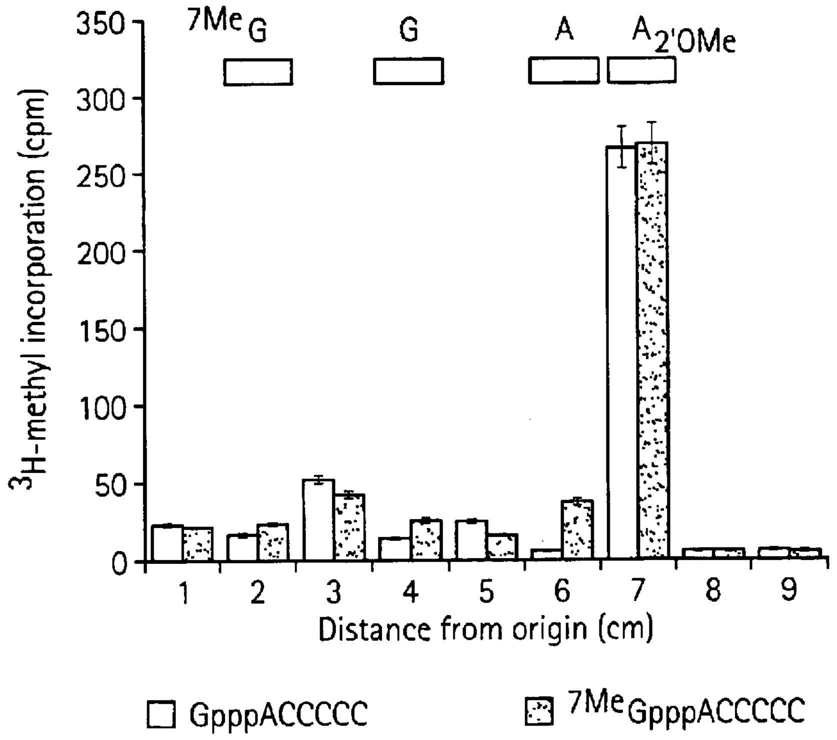

FIG. 6 concerns the MTase activity. (A) Assay of the MTase activity. The extent of methyl transfer from Ado [methyl-$^{3}$H]Met to three different RNA substrates (pppACCCCC, GpppACCCCC and $^{7Me}$GpppACCCCC) by 5 μg of CEF is plotted as a function of time. Data points represent averages of three independent experiments and are presented as percentage of [methyl-$^3$H] incorporation. The plateau of 100% incorporation represents a concentration of 1.5 $\mu$M transferred methyl groups in the reaction at the final reaction time. (B) Identification of the nucleoside methylated by CEF. RNAs incubated in the presence of Ado [methyl-$^3$H]Met and purified recombinant CEF were treated with phosphodiesterase and alkaline phosphatase, and analyzed using thin-layer chromatography. The experiment was performed independently twice. The figure shows a qualitative analysis of one chromatogram. Indicated positions of marker nucleosides (N7-methylated guanosine ($^{7Me}$G), guanosine (G), adenosine (A) and 2'-O-methylated adenosine ($A_{2'OMe}$)) were determined under UV light.

I. Identification of the *Flavivirus* Capping Enzyme.

The Capping Enzyme of *Flaviviridae*, designated CEF, is a thirty-three kDa N-terminal domain of the RNA-dependent RNA polymerase of the Dengue virus type 2 (New Guinea). The CEF was produced in a soluble form in *E. coli* and purified. This domain possesses several signature sequences typical of SAM-binding proteins (14). We discovered that it is a 2'-O-methyltransferase (13). However, when $\alpha$-$^{32}$P-GTP is incubated in the presence of CEF and subsequently UV-irradiated, the radiolabel remains bound to the protein whether or not magnesium is present in the reaction (as shown in FIG. 1A, lanes 1, 2, and 5). $\alpha$-$^{32}$P-ATP is unable to label CEF significantly under similar conditions (lanes 3 and 4). The amino acid substitution F25A abolishes UV-mediated labeling, thereby indicating that F25 might play a role in GTP-binding (lanes 5 and 6). In the presence of magnesium, CEF can be labeled without UV-irradiation, although to a lesser extent ($\approx$13-fold) (as shown in FIG. 1B, lane 1). This labeling is resistant to various chemical treatments as well as to boiling in SDS-containing buffer, indicating that the observed binding might be covalent. Interestingly, the presence of Ribavirin 5'-triphosphate is able to decrease GTP-binding to CEP, indicating that this analogue might compete for the GTP binding site (lanes 1–6). This labeling depends on the presence of magnesium. These results suggest that CEF is the Dengue virus guanylyltransferase.

II. Methyltransferase Activity Assay.

The enzymatic MTase activity of NS5MTase$_{DV}$ was assayed by following the transfer of a radiolabeled methyl group from AdoMet to various RNA substrates using a filter-binding assay. Capped and non-capped short RNA substrates (GpppACCCCC, $^{7Me}$GpppACCCCC and pppACCCCC) were used as methyl acceptors. As shown in FIG. 4A, the protein is able to transfer a methyl group from AdoMet to the capped RNA subtrates GpppACCCCC and $^{7Me}$GpppACCCCC, but not to the non-capped substrate pppACCCCC. Methyltransfer to capped RNA occurs even when the N7-position of the guanine is already methylated.

To characterize the methylated nucleoside(s), the reaction mixture was treated with phosphodiesterase which cleaves both RNA and cap structure, and alkaline phosphatase to render the nucleoside components. Separation of the reaction products using thin-layer chromatography shows (FIG. 6B) that most of the radioactivity co-migrates with 2'-O-methylated adenosine ($A_{2'OMe}$), and not with N7-methylated guanosine ($^{7Me}$G). These results demonstrate that, under our experimental conditions, methylation occurs exclusively at the 2'-O-position of the second nucleotide. They do not exclude, however, that the N7-position of the guanine would be methylated by NS5MTase$_{DV}$ under conditions found in the replication complex in vivo. We conclude that NS5MTase$_{DV}$ is the 2'OMTase of the Dengue virus. The physical coupling of this domain to the polymerase domain is relevant to coordinating the initiation of genomic (+) RNA synthesis and RNA capping.

III. Structure of the CEF.

The crystal structure of CEF was determined by the multi-wavelength anomalous dispersion (MAD) method using a bound Hg ion as the anomalous scatterer (Table 1).

TABLE 1

Crystallization, data collection, structure solution and refinement statistics.

| Data set | | $Hg(CN)_2$ remote | $Hg(CN)_2$ peak | $Hg(CN)_2$ inflection | Native | Ribavirin triphosphate soak | GDPMP soak |
|---|---|---|---|---|---|---|---|
| Data collection | | | | | | | |
| Resolution range (Å) (last shell) | | 30–2.8 (2.95–2.8) | 30–2.8 (2.95–2.8) | 30–2.8 (2.95–2.8) | 30–2.4 (2.53–2.4) | 30–2.4 (2.53–2.4) | 30–2.8 (2.95–2.8) |
| Wavelength (Å) | | 0.83211 | 1.00474 | 1.00850 | 0.933 | 0.933 | 0.933 |
| Number of reflections | | 10159 | 10220 | 10198 | 16248 | 15246 | 10263 |
| Rsym (%) | | 6.1 | 5.5 | 8.1 | 5.1 | 6.8 | 4.4 |
| (last shell) | | (30.4) | (24.5) | (30.5) | (35.8) | (44.5) | (40.2) |
| Completeness (%) | | 99.7 | 99.9 | 99.8 | 99.6 | 94.7 | 99.0 |
| (last shell) | | (99.7) | (99.9) | (99.8) | (99.6) | (94.7) | (99.0) |
| Multiplicity | | 4.9 | 7.0 | 7.0 | 5.5 | 2.3 | 4.0 |
| (last shell) | | (3.9) | (6.2) | (6.1) | (5.2) | (2.1) | (3.8) |
| MAD analysis | | | | | | | |
| Number of sites | 1 | | | | | | |
| Phasing power (acentrics/centric) | | | 0.91/0.77 | 0.61/0.47 | | | |
| Rcullis (acentrics/centric) | | | 0.87/0.86 | 0.96/0.94 | | | |
| Rcullis | | | 0.89 | 0.95 | | | |
| FOMmlphare (30–2.8 Å) | 0.36 | | | | | | |
| FOMdm (30–2.4 Å) | 0.87 | | | | | | |

TABLE 1-continued

Crystallization, data collection, structure solution and refinement statistics.

| Data set | $Hg(CN)_2$ remote | $Hg(CN)_2$ peak | $Hg(CN)_2$ inflection | Native | Ribavirin triphosphate soak | GDPMP soak |
|---|---|---|---|---|---|---|
| Refinement statistics | | | | | | |
| Resolution range (Å) | | | | 30–2.4 | 30–2.4 | 30–2.8 |
| Number of Reflections (F > 0) | | | | 16049 | 15239 | 10251 |
| Rcryst | | | | 23.6 | 22.5 | 21.9 |
| Rfree | | | | 25.0 | 24.6 | 25.0 |
| Rms deviations | | | | | | |
| Bonds (Å) | | | | 0.009 | 0.007 | 0.008 |
| Angles (°) | | | | 1.485 | 1.377 | 1.418 |

Rsym=S|I−<I>|/SI. Rcullis =S|E|/S|DF|.

Phasing power=(rms Fh)/(rms E), where Fh is the heavy atom structure amplitude and E is the residual lack of closure.

Rcryst=S||Fobs|−|Fcalc||/S|Fobs|. All data were used with no sigma cutoff.

Rfree=S||Fobs|−|Fcalc||/S|Fobs|, where Fobs are test set amplitudes (5% of the data) not used in the refinement.

Crystals were grown at room temperature in hanging drops. 1 μl of the protein solution (12 mg/ml) was mixed with 1 μl of a reservoir solution containing 0.1 M sodium citrate, pH 5.8, 1.2 M lithium sulfate, and 0.5 M ammonium sulfate, and allowed to equilibrate by vapor diffusion over one week. Crystals were cryoprotected in the same solution containing 20% glycerol, and flash-frozen in a nitrogen stream. Crystals grew in space group $P3_121$ (a=111.5 Å, c=56.3 Å). Data were collected at the ESRF on beamlines ID14-2, ID14-3 and BM14 using charge-coupled device detectors (ADSC Q4 or MAR 165). Images were processed using DENZO (22), and intensities were merged with SCALA (23). MAD datasets were collected using a Hg(CN) 2-soaked crystal. Phases were calculated using MLPHARE (23). Solvent flattening and phase extension to 2.4 Å were performed using DM (24). Residues 10 to 261 could be built and assigned unambiguously in the initial density map. Several rounds of slow-cooled torsion molecular dynamics refinement and model improvement were carried out using CNS (25) and TURBO (26). Rfree (27) was calculated using 5% of the unique data.

Residues 7 to 264 were defined in the structure and constitute the final model using Dengue NS5 sequence numbering. CEF presents an overall globular structure made of three subdomains (as shown in FIGS. 2A and 2B). They are a N-terminal module (subdomain 1, residues 1 to 70), a SAM-binding core (subdomain 2, residues 71 to 222), and a C-terminal sequence (subdomain 3, residues 223 to 264) located between subdomains 1 and 2, and forming the bottom of a narrow cleft. Subdomain 1 has no known homologue out of the *Flaviviruses*, nor does it share a common structural feature with any protein structure deposited in the Protein Data Bank as determined using the DALI server (15). It starts with a helix A1-turn-helix A2 motif and constitutes one side of the cleft separating subdomain I from the core domain of CEF. The core subdomain 2 folds like a typical SAM-dependent methyltransferase domain homologous to that of Reovirus λ2 (5) and vaccinia virus VP39 enzyme (16). This core is comprised of a twisted mixed b-sheet comprising 7 b-strands (b1 to b7) and 5 helices (a1 to a5). This structural homology allows one to superimpose the core of CEF onto the related VP39 nucleoside-2'-O-methyltransferase domain in complex with both SAM and mRNA cap (17). An additional density was found in the difference Fourier map within CEF subdomain 2 in the vicinity of the cleft. The superimposition of VP39 and CEF showed that this density is located in the SAM-binding pocket of the VP39 methyltransferase. It was identified and refined as a bound S-adenosyl-L-homocysteine (SAHC) molecule, the product of the methyl transfer reaction, which probably originated from *E. coli* and co-purified with CEF. The adenine base of the SAHC molecule is held tightly in a pocket lined by 4 b-strands as found in other SAM-dependent methyltransferases. The sulfur atom of SAHC points toward the cleft. The CEF cleft occupies the same location as the RNA-binding cleft seen in the VP39 nucleoside-2'-O-methyltransferase structure. Surface potential analysis shows that the bottom of the CEF cleft is positively charged, indicating that it might also accommodate the negatively charged phosphates of the 5'-mRNA end (as shown in FIG. 2C). The Applicant demonstrated that this surface potential and the topological similarity with VP39 support that CEF might be a nucleoside-2'-O-methyltransferase acting to produce a cap 1 structure.

Examination of the crystal packing showed that there is enough space in the crystals for diffusion of small molecules such as nucleotides. When soaked in a solution containing b,g-methylene GTP (GDPMP), a non-hydrolysable GTP analogue, no obvious rearrangement occurred in the crystal packing. A calculated difference Fourier map showed an additional density corresponding to the GTP analogue molecule bound to subdomain 1 (as shown in FIG. 3A). The base, ribose hydroxyl, and a-phosphate moieties of the GTP analogue contact mainly helices A1 and A2. Curiously, the sequence of the turn between A1 and A2 shares 79% homology with that of a P-loop, a typical nucleotide binding motif (18). However, the GTP-binding mode to this loop is totally different from that of nucleotides to P-loops because the phosphates of GTP do not contact the loop. Instead, phosphates point away from the loop towards the cleft, and they interact with residues belonging to the core domain at the bottom of the cleft. The ribose adopts a Northern configuration, and specificity for ribonucleotides is achieved by two hydrogen-bonds with the 2'-OH involving $Lys^{14}$ and $Asn^{18}$ side-chains, conserved amongst *Flaviviruses.* Amino acid side-chains closest to the a-phosphate are those of $Lys^{29}$ and $Ser^{150}$. As the West Nile virus protein domain corresponding to CEF (67% amino acid identity and 87% similarity in 296 residues) has a conserved arginine at position 29 (as shown in FIG. 2B), the chemical mechanism of the guanylyltransferase reaction remains undetermined. The $Ser^{150}$ side-chain contacts oxygen atoms from both a- and b-phosphate groups. $Ser^{150}$ belongs to a strand connecting b4 to helix a6 against which packs the GTP-binding site of subdomain 1.

IV. Significance of the CEF Structure.

The structural organization of the GTP-binding site is remarkable. It can be viewed as a modular extension (residues 7 to 70) of a conserved SAM-/RNA-binding domain (residues 71 to 222). This N-terminal appendage creates a novel GTP-binding site of previously unreported fold, making CEF the smallest bifunctional capping enzyme known, and defining a type of guanylyltransferase distinct from both the Reovirus 12 guanylyltransferase and those belonging to the covalent nucleotidyl transferase family. As the close association of guanylyltransferase and methyltransferase activities is a characteristic of many viral capping systems, this type of modular extension of SAM-IRNA-binding domain might be found in other viruses for which guanylyltransferases have yet to be identified (6).

There are a number of original structural features of CEF that differ from known nucleotide binding site structures, exemplified by the contacts made by the purine base. The guanine specificity is achieved via three specific interactions of main-chain carbonyl groups with the 2-amino group of guanine (as shown in FIG. 3B). None of these interactions would be possible with adenine. Thus, the specificity for guanine vs. adenine binding does not involve specific interactions of the protein with the C6 purine substituent. This type of nucleotide discrimination appears to be novel. The N7 position of guanine points towards the solvent and does not contact any residue. This is different from the VP39 enzyme for which the alkylated base is a determinant of binding specificity (19).

Ribavirin 5'-triphosphate binds to CEF under the same conditions as those used for the GTP analogue, and makes the same contacts as the GTP analogue (as shown in FIG. 4A). Interestingly, the carbonyl group of Ribavirin does not interact with any residue, but the $NH_2$ group hydrogen-bonds the same carbonyl groups of $Leu^{17}$, $Asn^{18}$, and $Leu^{20}$ as the $NH_2$ of the GTP analogue (compare FIGS. 3A and 4A). Thus, Ribavirin does not seem to be structurally discriminated. Although the structural resemblance of Ribavirin with guanosine originates from the spatial position of both 1- and 6-positions, this mimicry is at odds with the binding mode of Ribavirin (compare FIGS. 3B and 4B). It is the $NH_2$ of Ribavirin, not its carbonyl group, which adopts a spatially equivalent position to that of the 2-amino group of guanine.

Ribavirin 5'-triphosphate exhibits CEF-binding affinity similar to that of GTP (FIG. 1). In Ribavirin-treated cells, the concentration of Ribavirin 5'-triphosphate is at least about one order of magnitude lower than that of GTP (20). Therefore, the antiviral effect of Ribavirin cannot be explained without the down-regulation of the intracellular GTP pool through inhibition of IMP-DH by Ribavirin 5'-monophosphate. Since RNA capping is essential for various viruses (6), the structural mechanism for Ribavirin inhibition of RNA capping presented here might account for the antiviral activity of Ribavirin against *Flaviviruses*, but does not exclude the inhibition of additional viral enzymatic activities. For example, Ribavirin 5'-triphosphate is incorporated into Poliovirus during viral RNA polymerization (21). However, in the absence of interferon, Ribavirin nucleotides do not exert an antiviral activity against the *Flaviviridae* Hepatitis C virus, which has no RNA capping activity. Thus, the antiviral activity of Ribavirin against *Flaviviruses* might be dependent on inhibition cellular IMP-DH and, at least, viral capping.

Together with the adenine/guanine specificity, the Ribavirin binding mode has two important consequences in terms of drug design. First, examination of nucleotide-binding protein structures in the Protein Data Bank indicates that no specific recognition of GTP with the purine 2-position only (as shown in FIG. 3B) has been reported before. Cellular NTP-binding enzymes appear to contact at least two of the purine 1-, 2-, or 6-positions. If this holds true, our results explain the apparent lack of significant affinity of Ribavirin nucleotides for cellular GTP-binding proteins, a finding consistent with Ribavirin antiviral selectivity. The second issue is that of drug-resistance. Since only main-chain contacts are involved in the binding of Ribavirin, a mere substitution of an amino acid side-chain directly involved in the discrimination of Ribavirin relative to GTP is unlikely. Consequently, drug-resistance by such a direct mechanism is also unlikely. These structural features provide a unique basis for a rational drug-design against many human pathogens of viral origin, of which the emerging *Flaviviruses* are a timely example.

V. Process of Testing Drugs with Antiviral Properties.

The CEF protein and its ability to bind nucleotide analogue, such as ribavirin 5'-triphosphate, can be used to probe any inhibitor. The identified inhibitors are useful in treatment of diseases caused by *Flavivirus* infection. The selection of acyclovir 5'-triphosphate as an inhibitor is exemplified below.

Acyclovir is a nucleoside analogue used in the treatment of Herpesvirus infections. These viruses encode their own nucleoside kinase able to phosphorylate acyclovir into acyclovir 5'-monophosphate. Any herpesvirus-infected cell is then able to perform this phosphorylation reaction, whereas an uninfected cell is not, resulting in a good selectivity for activation of the drug. Cellular kinases are then able to phosphorylate acyclovir 5'-monophosphate up to acyclovir 5'-triphosphate, which is a good inhibitor of Herpesvirus polymerase.

Because most viruses (except Herpes viruses) do not possess the viral nucleoside kinase, acyclovir cannot be activated to the monophosphate state and hence, no acyclovir 5'-triphosphate can be produced to inhibit viral growth. Acyclovir is thus an inactive drug against these viruses, but it is not known whether the polymerase or any other viral enzyme, such as the capping enzyme of these viruses could be inhibited by acyclovir 5'-triphosphate.

The CEF protein and its ability to bind GTP provides an easy way to determine the potential inhibitory power of any nucleoside acting as a competitive inhibitor of GTP, such as the guanosine analogue acyclovir 5'-triphosphate.

The binding affinity constant of GTP to CEF can be easily determined using a fixed concentration of CEF and increasing concentrations of radiolabeled GTP as described in FIG. 1A. The CEF.GTP complex is assayed using UV-crosslinking, and plotted as a function of GTP concentration. This complex becomes saturated at high GTP concentrations, following a hyperbolic saturation function from which a binding affinity constant Kd of 52 $\mu$M can be determined.

In order to determine the binding affinity of acyclovir 5'-triphosphate relative to that of GTP, CEF is first incubated with about 52 $\mu$M of GTP, and increasing concentrations of acyclovir 5'triphosphate are added to the reaction. The CEF-GTP complex is then assayed using UV-crosslinking as described above. If acyclovir 5'triphosphate competes with radiolabeled GTP for the CEF active-site, acyclovir 5'triphosphate will replace GTP in the active-site. Because acyclovir 5'-triphosphate is not labeled, one will observe a decreased amount of radiolabeled CEF-GTP complex, from which a relative binding affinity constant of about 79 $\mu$M for the acyclovir 5'-triphosphate binding to CEF can be determined (see FIG. 1B).

In this case, the important information extracted from this test is that although acyclovir may not be active against a given virus, the triphosphate form of acyclovir is a good inhibitor of the CEF enzyme. Hence, the information extracted from this test is that any vectorized form of acyclovir 5'monophosphate that might by-pass the first nucleoside kinase activation step, which restricts the antiviral activity to Herpesviruses, should result in having acyclovir 5'-triphosphate produced in the cell. The acyclovir 5'-triphosphate should then inhibit any virus having an essential enzyme such as CEF, as determined by the CEF-acyclovir 5'-triphosphate binding assay.

It is clear that this kind of assay can be used with any molecule (nucleoside or non-nucleoside) to CEF in the GTP binding site. The simplicity, robustness, and the fact that thijs assay can be performed a single-tube are indicative that this CEF-binding assay can be used to screen rapidly and efficiently potential inhibitors of enzymes such as the CEF protein.

References

The following publications are hereby incorporated by reference in their entireties.

1. C. A. Beelman, et al., Nature 382, 642–6 (1996).
2. S. Shuman, Prog. Nucleic Acid Res. Mol. Biol. 66, 1–40 (2000).
3. S. Shuman, B. Schwer, Mol. Microbiol. 17, 405–10 (1995).
4. K. Hakansson, A. J. Doherty, S. Shuman, D. B. Wigley, Cell 89, 545–53 (1997).
5. K. M. Reinisch, M. L. Nibert, S. C. Harrison, Nature 404, 960–7 (2000).
6. M. Bisaillon, G. Lemay, Virology 236, 1–7 (1997).
7. R. W. Sidwell, et al., Science 177, 705–706 (1972).
8. J. L. Patterson, R. Fernandez-Larsson, Rev. Infectious Dis. 12, 1139–1146 (1990).
9. I. Jordan, T. Briese, N. Fischer, J. Y. Lau, W. I. Lipkin, J. Infect. Dis. 182, 1214–7 (2000).
10. J. Neyts, A. Meerbach, P. McKenna, E. De Clercq, Antiviral Res. 30, 125–32 (1996).
11. J. F. Anderson, et al., Science 286, 2331–2333 (1999).
12. T. J. Chambers, C. S. Hans, R. Galler, C. M. Rice, Ann. Rev. Microbiol. 44, 649–688 (1990).
13. The CEF encoding gene was cloned from the genomic RNA of Dengue virus type 2 (New Guinea) using RT-PCR into the bacterial expression vector pQE30. The authentic amino acid sequence of NS5 was preceded by the sequence tag MRSG$(H)_6$ to help purification of CEF which comprised a total of 306 residues. Expression was at 30° C., and CEF was purified from the soluble fraction using Ni-Agarose affinity chromatography followed by anion-exchange chromatography (SP-column, Pharmacia) in Bicine buffer, pH 7.5, 0.3 M NaCl, 1 mM DTT, 10% glycerol. CEF binds single-stranded RNA (D. Benarroch, M. P. Egloff, B. Selisko, J. L. Romette, B. Canard, EMBO J, 21,11, pp2757–2768 (2002).
14. E. V. Koonin, J. Gen. Virol. 74, 733–740 (1993).
15. L. Holm, C. Sander, J. Mol. Biol. 233, 123–38 (1993).
16. A. E. Hodel, P. D. Gershon, X. Shi, F. A. Quiocho, Cell 85, 247–56 (1996).
17. A. E. Hodel, P. D. Gershon, F. A. Quiocho, Mol. Cell 1, 443–7 (1998).
18. M. Saraste, P. R. Sibbald, A. Wittinghofer, Trends Biochem. Sci. 15, 430–4 (1990).
19. F. A. Quiocho, G. Hu, P. D. Gershon, Curr. Opin. Struct. Biol. 10, 78–86 (2000).
20. A. Kornberg, T. A. Baker, . (W.H. Freeman & Co., 1992) pp. 54.
21. S. Crotty, et al., Nat. Med. 6, 1375–9 (2000).
22. Z. Otwinowski, W. Minor, Methods Enzymol. 276, 307–326 (1997).
23. CCP4, Acta Crystallogr. D 50, 760–763 (1994).
24. K. Cowtan, Joint CCP4 and ESF-EACBM Newsletter on Protein Crystallography 31, 34–38 (1994).
25. A. T. Brünger, et al., Acta Crystallogr. D 54, 905–921 (1998).
26. A. Roussel, C. Cambillau, in Silicon Graphics Directory S. Graphics, Ed. (Mountain View, Calif., 1991) pp. 97.
27. A. T. Brünger, Nature 355, 472–474 (1992).
28. P. J. Kraulis, J. Appl. Cryst. 24, 946–950 (1991).
29. E. A. Merrit, M. E. P. Murphy, Acta Crystallogr. D Biol. Crystallogr. 50, 869–873 (1994).
30. A. Nicholls, K. A. Sharp, B. Honig, Proteins 11, 281–296 (1991).

What is claimed:

1. An isolated and purified capping enzyme of *flavivirus* (CEF) capable of acting as an guanylyltransferase and methyltransferase consisting essentially of a polypeptide from the N-terminus of *flavivirus* genus RNA-dependent RNA polymerase.

2. The capping enzyme of *flavivirus* (CEF) according to claim 1, wherein said polypeptide has a three-dimensional structure and comprises a N-terminal module (subdomain 1), a SAM-binding core (subdomain 2), and a C-terminal sequence (subdomain 3) located between subdomains 1 and 2 in the three-dimensional structure of the polypeptide, and forming a bottom portion of a narrow cleft.

3. The capping enzyme of *flavivirus* (CEF) according to claim 2, wherein said subdomain 1 starts with a helix A1-turn-helix A2 motif.

4. The capping enzyme of *flavivirus* (CEF) according to claim 2, wherein said subdomain 2 comprises a twisted mixed β-sheet comprising 7 β-strands and 5 helices.

5. The capping enzyme of *flavivirus* (CEF) according to claim 2, wherein said subdomain 3 is positively charged.

6. The capping enzyme of *flavivirus* (CEF) according to claim 1, wherein said CEF is a polypeptide comprising SEQ ID No. 1.

7. The capping enzyme of *flavivirus* (CEF) according to claim 1, wherein said CEF is a polypeptide comprising SEQ ID No. 2.

8. The capping enzyme of *flavivirus* (CEF) according to claim 1, wherein said CEF is a polypeptide comprising SEQ ID No. 3.

9. The isolated and purified capping enzyme of *flavivirus* (CEF) of claim 1, wherein the polypeptide is about 33 kDa.

10. The isolated and purified capping enzyme of *flavivirus* (CEF) of claim 1, wherein the RNA-dependent RNA polymerase is a Dengue, Yellow Fever or West Nile virus RNA-dependent RNA polymerase.

11. A method for determining inhibitory power of a biologically active compound acting as a competitive inhibitor of GTP comprising:

a) incubating CEF according to claim 1 with radiolabeled GTP;

b) adding selected different concentrations of said biologically active compound;

c) assaying resulting radiolabeled CEF-GTP complex produced from step a);

d) quantifying an amount of radiolabeled CEF-GTP complex produced from step c);

e) comparing said amount to a binding affinity constant of GTP to CEF; and f) determining said inhibitory power of said biologically active compound.

12. The method according to claim 11, wherein the concentration at which said incubating is conducted at about 52 μM of GTP.

13. The method according to claim 12, wherein said selected different concentrations of GTP are selected from the group consisting of about 0 μM, about 10 μM, about 20 μM, about 50 μM, about 100 μM, about 200 μM, about 300 μM, about 500 μM, and about 800 μM.

14. The method according to claim 11, wherein said assaying comprises UV-crosslinking $\alpha$-$^{32}$P-GTP to CEF.

15. A method for selecting an inhibitory biologically active compound capable of reducing CEF binding to GTP as an antiviral pharmaceutical agent according to claim 11, further comprising:

selecting biologically active compounds with a binding affinity higher than the binding affinity constant of GTP to CEF.

16. A method according to claim 11, wherein the biologically active compound is a nucleoside or nucleoside analogue.

* * * * *

SEQUENCE LISTING

```
<160> NUMBER OF SEQ ID NOS: 3

<210> SEQ ID NO 1
<211> LENGTH: 264
<212> TYPE: PRT
<213> ORGANISM: Dengue virus type 2

<400> SEQUENCE: 1

Gly Thr Gly Asn Ile Gly Glu Thr Leu Gly Glu Lys Trp Lys Ser Arg
  1               5                  10                  15

Leu Asn Ala Leu Gly Lys Ser Glu Phe Gln Ile Tyr Lys Lys Ser Gly
             20                  25                  30
```

-continued

Ile Gln Glu Val Asp Arg Thr Leu Ala Lys Glu Gly Ile Lys Arg Gly
35 40 45

Glu Thr Asp His His Ala Val Ser Arg Gly Ser Ala Lys Leu Arg Trp
50 55 60

Phe Val Glu Arg Asn Leu Val Thr Pro Glu Gly Lys Val Val Asp Leu
65 70 75 80

Gly Cys Cys Arg Gly Gly Trp Ser Tyr Tyr Cys Gly Gly Leu Lys Asn
85 90 95

Val Arg Glu Val Lys Gly Leu Thr Lys Gly Gly Pro Gly His Glu Glu
100 105 110

Pro Ile Pro Met Ser Thr Tyr Gly Trp Asn Leu Val Arg Leu Gln Ser
115 120 125

Gly Val Asp Val Phe Phe Ile Pro Pro Glu Arg Cys Asp Thr Leu Leu
130 135 140

Cys Asp Ile Gly Glu Ser Ser Pro Asn Pro Thr Val Glu Ala Gly Arg
145 150 155 160

Thr Leu Arg Val Leu Asn Leu Val Glu Asn Trp Leu Ser Asn Asn Thr
165 170 175

Gln Phe Cys Val Lys Val Leu Asn Pro Tyr Met Ser Ser Val Thr Glu
180 185 190

Lys Met Glu Ala Leu Gln Arg Lys Phe Gly Gly Ala Leu Val Arg Asn
195 200 205

Pro Leu Ser Arg Asn Ser Thr His Glu Met Tyr Trp Val Ser Asn Ala
210 215 220

Ser Gly Asn Ile Val Ser Ser Val Asn Met Ile Ser Arg Met Leu Ile
225 230 235 240

Asn Arg Phe Thr Met Arg His Lys Lys Ala Thr Tyr Glu Pro Asp Val
245 250 255

Asp Leu Gly Ser Gly Thr Arg Asn
260

<210> SEQ ID NO 2
<211> LENGTH: 267
<212> TYPE: PRT
<213> ORGANISM: West Nile virus

<400> SEQUENCE: 2

Arg Gly Gly Ala Lys Gly Arg Thr Leu Gly Glu Val Trp Lys Glu Arg
1 5 10 15

Leu Asn Glu Met Thr Lys Glu Glu Phe Thr Arg Tyr Arg Lys Glu Ala
20 25 30

Ile Ile Glu Val Asp Arg Ser Ala Ala Lys His Ala Arg Arg Glu Gly
35 40 45

Asn Ile Thr Gly Gly His Pro Val Ser Arg Gly Thr Ala Lys Leu Arg
50 55 60

Trp Leu Val Glu Arg Arg Phe Leu Glu Pro Val Gly Lys Val Val Asp
65 70 75 80

Leu Gly Cys Gly Arg Gly Gly Trp Cys Tyr Tyr Met Ala Thr Gln Lys
85 90 95

Arg Val Gln Glu Val Lys Gly Tyr Thr Lys Gly Gly Pro Gly His Glu
100 105 110

Glu Pro Gln Leu Val Gln Ser Tyr Gly Trp Asn Ile Val Thr Met Lys
115 120 125

-continued

```
Ser Gly Val Asp Val Phe Tyr Arg Pro Ser Glu Ala Ser Asp Thr Leu
    130                 135                 140

Leu Cys Asp Ile Gly Glu Ser Ser Ser Ser Ala Glu Val Glu Glu His
145                 150                 155                 160

Arg Thr Val Arg Val Leu Glu Met Val Glu Asp Trp Leu His Arg Gly
                165                 170                 175

Pro Lys Glu Phe Cys Ile Lys Val Leu Cys Pro Tyr Met Pro Lys Val
            180                 185                 190

Ile Glu Lys Met Glu Ile Leu Gln Arg Arg Tyr Gly Gly Gly Leu Ile
        195                 200                 205

Arg Asn Pro Leu Ser Arg Asn Ser Thr His Glu Met Tyr Trp Val Ser
    210                 215                 220

His Ala Ser Gly Asn Ile Val His Ser Val Asn Met Thr Ser Gln Val
225                 230                 235                 240

Leu Leu Gly Arg Met Glu Lys Lys Thr Trp Lys Gly Pro Gln Phe Glu
                245                 250                 255

Glu Asp Val Asn Leu Gly Ser Gly Thr Arg Ala
            260                 265


<210> SEQ ID NO 3
<211> LENGTH: 266
<212> TYPE: PRT
<213> ORGANISM: Yellow fever virus

<400> SEQUENCE: 3

Arg Gly Ser Ala Asn Gly Lys Thr Leu Gly Glu Val Trp Lys Arg Glu
  1               5                  10                  15

Leu Asn Leu Leu Asp Lys Arg Gln Phe Glu Leu Tyr Lys Arg Thr Asp
             20                  25                  30

Ile Val Glu Val Asp Arg Asp Thr Ala Arg Arg His Leu Ala Glu Gly
         35                  40                  45

Lys Val Asp Thr Gly Val Ala Val Ser Arg Gly Thr Ala Lys Leu Arg
     50                  55                  60

Trp Phe His Glu Arg Gly Tyr Val Lys Leu Glu Gly Arg Val Ile Asp
 65                  70                  75                  80

Leu Gly Cys Gly Arg Gly Gly Trp Cys Tyr Tyr Ala Ala Ala Gln Lys
                 85                  90                  95

Glu Val Ser Gly Val Lys Gly Phe Thr Leu Gly Arg Asp Gly His Glu
            100                 105                 110

Lys Pro Met Asn Val Gln Ser Leu Gly Trp Asn Ile Ile Thr Phe Lys
        115                 120                 125

Asp Lys Thr Asp Ile His Arg Leu Glu Pro Val Lys Cys Asp Thr Leu
    130                 135                 140

Leu Cys Asp Ile Gly Glu Ser Ser Ser Ser Ser Val Thr Glu Gly Glu
145                 150                 155                 160

Arg Thr Val Arg Val Leu Asp Thr Val Glu Lys Trp Leu Ala Cys Gly
                165                 170                 175

Val Asp Asn Phe Cys Val Lys Val Leu Ala Pro Tyr Met Pro Asp Val
            180                 185                 190

Leu Glu Lys Leu Glu Leu Leu Gln Arg Arg Phe Gly Gly Thr Val Ile
        195                 200                 205

Arg Asn Pro Leu Ser Arg Asn Ser Thr His Glu Met Tyr Tyr Val Ser
    210                 215                 220
```

-continued

```
Gly Ala Arg Ser Asn Val Thr Phe Thr Val Asn Gln Thr Ser Arg Leu
225                 230                 235                 240

Leu Met Arg Arg Met Arg Arg Pro Thr Gly Lys Val Thr Leu Glu Ala
                245                 250                 255

Asp Val Ile Leu Pro Ile Gly Thr Arg Ser
            260                 265
```